Figure 1:
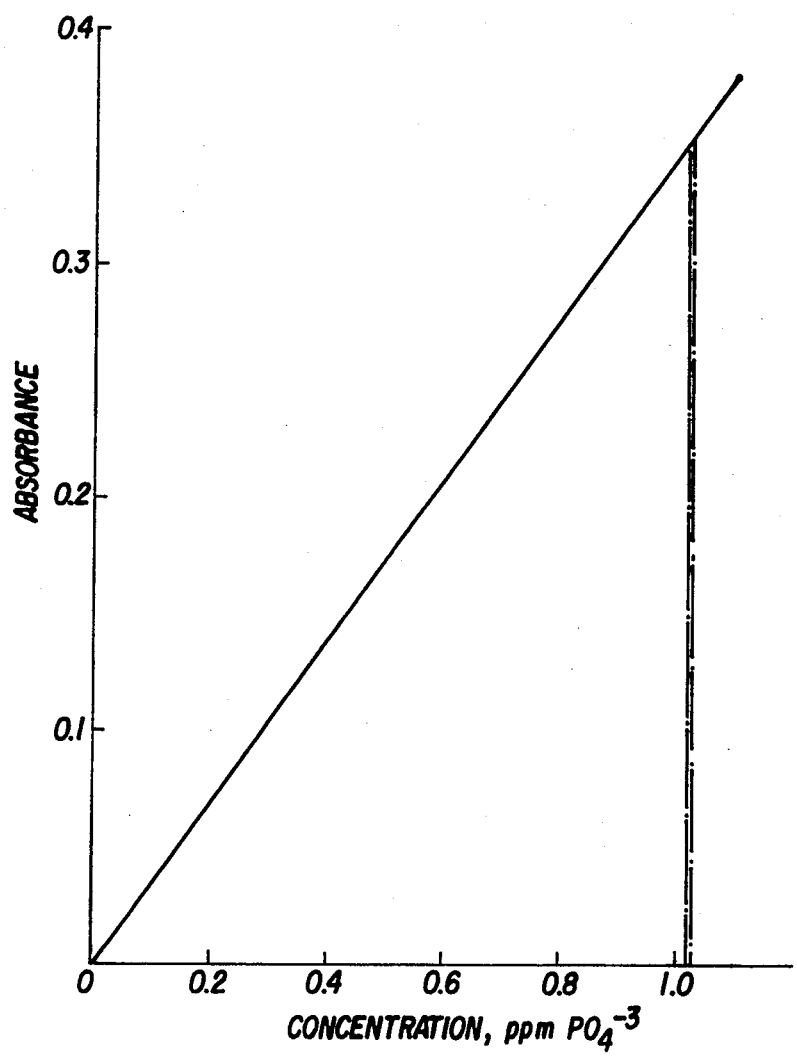

United States Patent [19]

Faust

[11] Patent Number: 4,544,639
[45] Date of Patent: Oct. 1, 1985

[54] PROCESS FOR DETERMINING THE AMOUNT OF ORGANIC PHOSPHONATE PRESENT IN AN AQUEOUS SOLUTION

[75] Inventor: Robert J. Faust, Pittsburgh, Pa.

[73] Assignee: Calgon Corporation, Pittsburgh, Pa.

[21] Appl. No.: 544,033

[22] Filed: Oct. 21, 1983

[51] Int. Cl.$^4$ ............................................. G01N 21/75
[52] U.S. Cl. ................................................... 436/104
[58] Field of Search ................................ 436/104–105; 422/15; 502/347

[56] References Cited

U.S. PATENT DOCUMENTS

| | | | |
|---|---|---|---|
| 3,336,221 | 8/1967 | Ralston | 210/700 |
| 3,393,150 | 7/1968 | Ralston | 210/700 |
| 3,431,217 | 3/1969 | Hwa | 252/389 R |
| 3,487,018 | 12/1969 | Trescinski | 210/699 |
| 3,886,204 | 5/1975 | Geffers et al. | 260/502.4 R |

OTHER PUBLICATIONS

Murphy et al., "A Modified Single Solution Method for the Determination of Phosphate in Natural Waters," *Analytic Chimica ACTA*, vol. 27, 1962, pp. 31–36.
Kitson et al., "Colorimetric Determination of Phosphorous a Molybdivanadophosphoric Acid," *Industrial and Engineering Chemistry*, (1944), vol. 16, No. 6, pp. 379–383.
Robertson, "Rapid Method for Est. of Total Phosphate in Water", *Jour. AWWA*, (1960), pp. 483–491.
Gefter, *Organophosphorus Monomers and Polymers* (1962), pp. IX–XIII.
Behrman, "The Thermal Decomposition of Peroxodisulfate Ions", *Review in Inorganic Chemistry* (1980), vol. 2, pp. 179–206.
Standard Method for the Examination of Water and Waste Water, 15th Edition, pp. 409–425.

*Primary Examiner*—Barry S. Richman
*Assistant Examiner*—John Donofrio
*Attorney, Agent, or Firm*—Michael C. Sudol; R. Brent Olson; William C. Mitchell

[57] ABSTRACT

The instant invention is directed to a process for determining the amount of organic phosphonate present in an aqueous solution, comprising the steps of:
(a) adding 1000 to 20,000 ppm of a strong oxidizing agent and 8 ppb to 5000 ppm silver ion to the aqueous solution;
(b) allowing the organic phosphonate present in said solution to react to form orthophosphate;
(c) precipitating any excess silver in said solution by the addition of 1000 to 50,000 ppm of a reducing agent or at least an equimolar amount of a halide, based on the silver ion added in Step (a), and removing any precipitate formed;
(d) adding to said solution 5 to 30 percent, by volume, of an acid solution containing 500 to 2000 ppm of ions selected from the group consisting of molybdate ion and vanadate ion, and if a halide was used in Step (c), adding 1000 to 50,000 ppm of a reducing agent;
(e) measuring the absorbance of said solution at 625 to 880 nanometers and determining the orthophosphate concentration from a calibration curve of orthophosphate concentration versus absorbance; and
(f) subtracting any orthophosphate present in the original aqueous solution from the orthophosphate concentration determined in Step (e), to give the total organic phosphonate concentration.

6 Claims, 4 Drawing Figures

PROCESS FOR DETERMINING THE AMOUNT OF ORGANIC PHOSPHONATE PRESENT IN AN AQUEOUS SOLUTION

BACKGROUND OF THE INVENTION

In order to treat water in aqueous systems with scale inhibitor, it is necessary to monitor the levels of organic phosphonate in the water so that the dosage of scale inhibitor necessary to inhibit phosphate-based scale, principally calcium phosphate, may be determined. The process presently used in the industry involves boiling the sample of water in the presence of acid and persulfate or digestion by ultraviolet light radiation in the presence of persulfate in order to convert organic phosphorus compounds to orthophosphate. The method of the instant invention does not require boiling or the use of special laboratory equipment for the conversion step.

A BRIEF DESCRIPTION OF THE DRAWINGS

Figure 2:
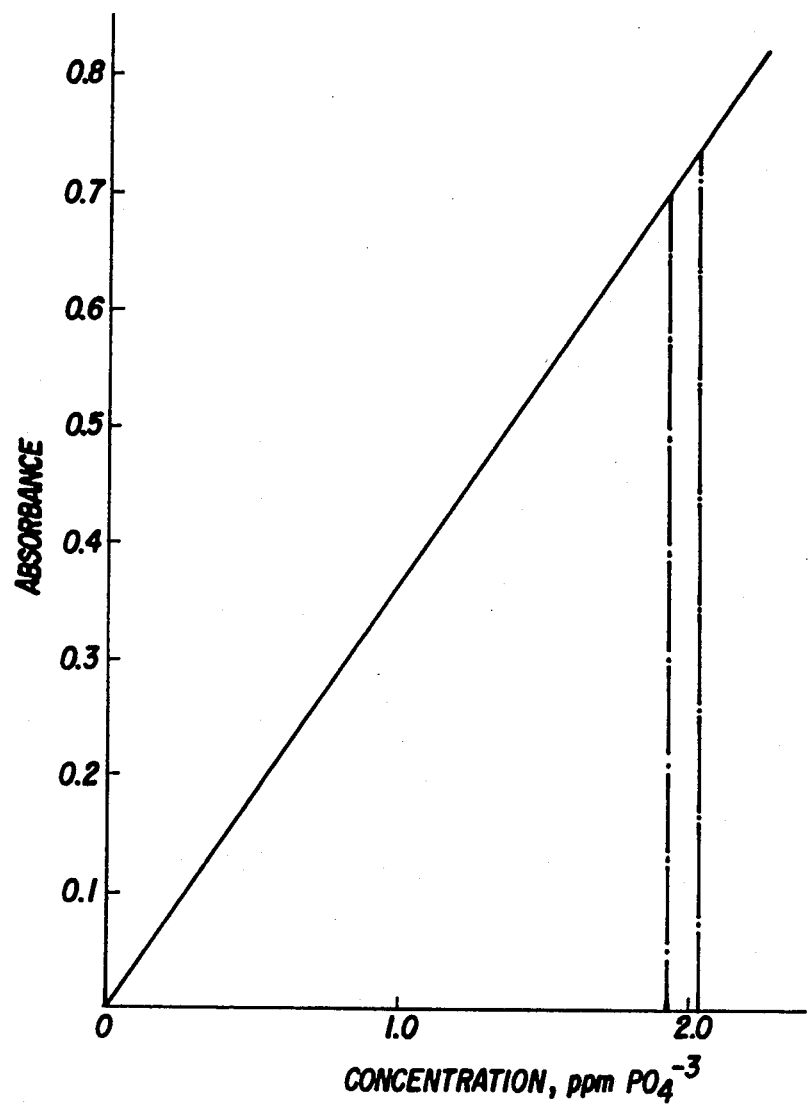
Figure 3:
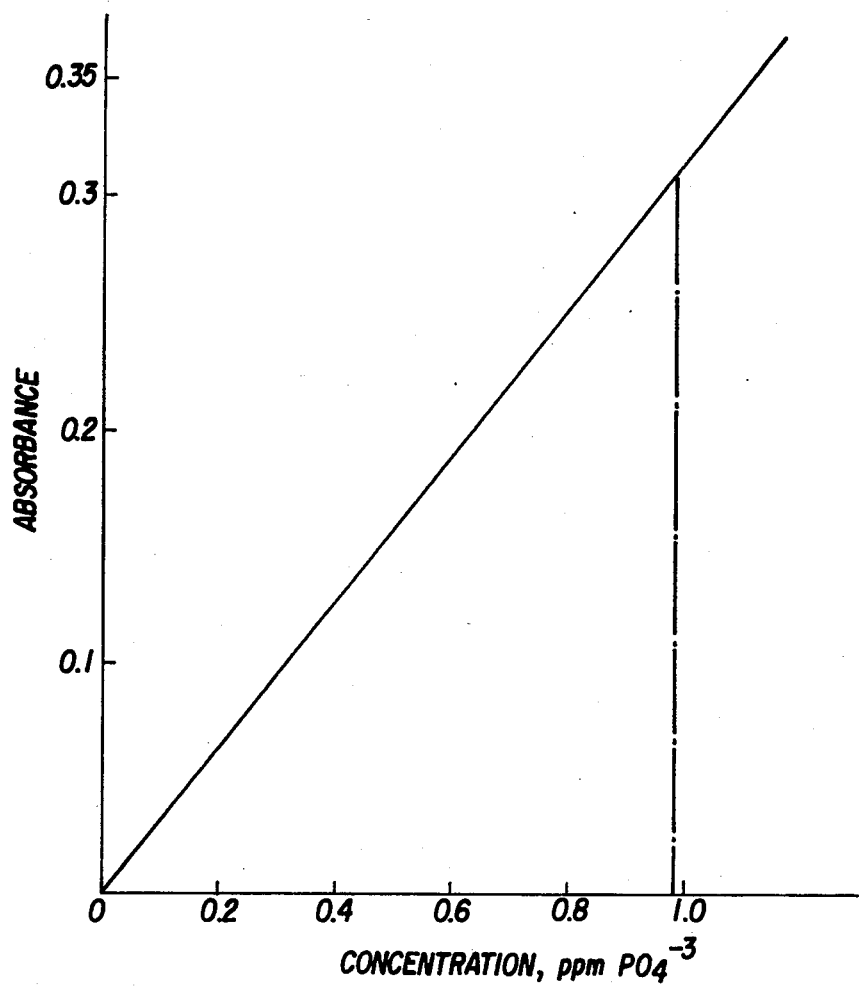
Figure 4:
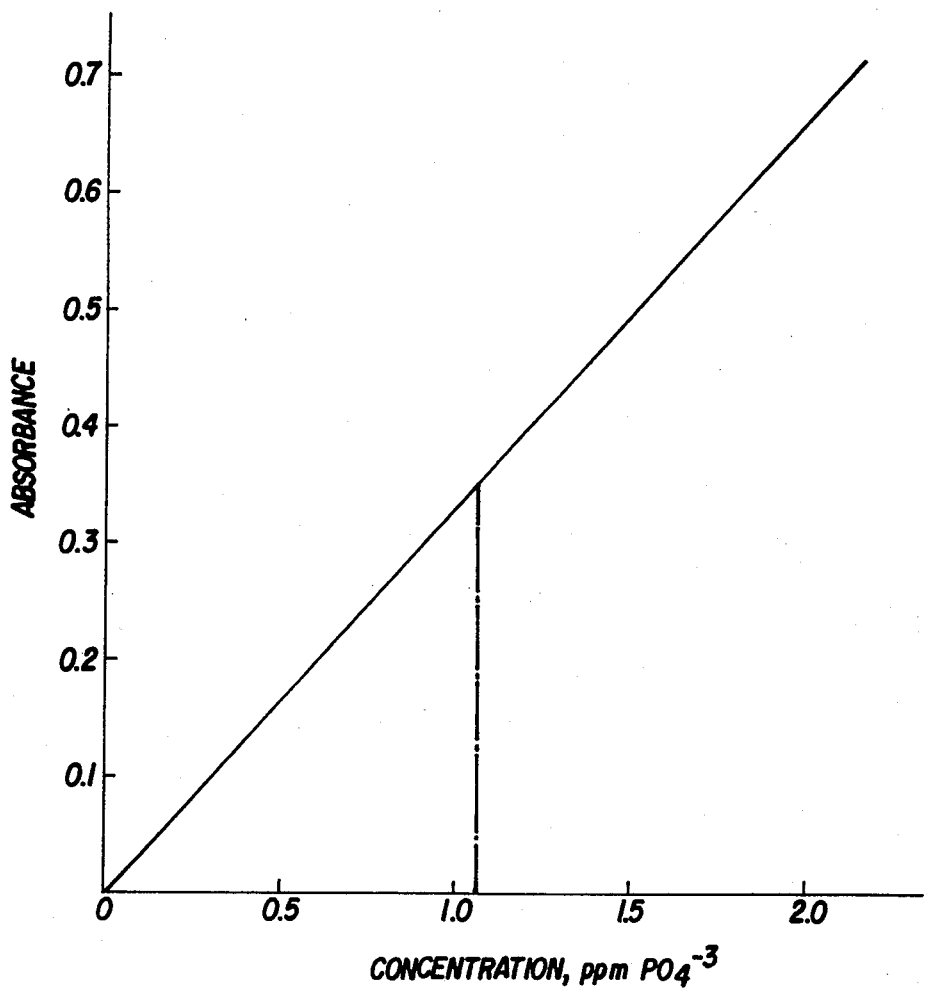

FIGS. 1 through 4 are the calibration curves of Examples 1 through 4, respectively.

DESCRIPTION OF THE INVENTION

The instant invention is directed to a process for determining the amount of organic phosphonate present in an aqueous solution, comprising the steps of:
(a) adding 1000 to 20,000 ppm of a strong oxidizing agent and 8 ppb to 5000 ppm silver ion to the aqueous solution;
(b) allowing the organic phosphonate present in said solution to react to form orthophosphate;
(c) precipitating any excess silver in said solution by the addition of 1000 to 50,000 ppm of a reducing agent or at least an equimolar amount of a halide, based on the silver ion added in Step (a), and removing any precipitate formed;
(d) adding to said solution 5 to 30 percent, by volume, of an aqueous acid solution containing 500 to 2000 ppm of ions selected from the group consisting of molybdate ion and vanadate ion, and if a halide is used in Step (c), adding 1000 to 50,000 ppm of a reducing agent;
(e) measuring the absorbance of said solution at 625 to 880 nanometers and determining the orthophosphate concentration from a calibration curve of orthophosphate concentration versus absorbance; and
(f) subtracting any orthophosphate present in the original aqueous solution from the orthophosphate concentration determined in Step (e), to give the total organic phosphonate concentration.

Organic phosphonate does not normally naturally occur in aqueous solutions. Phosphonates are added to control deposit and corrosion. Examples of organic phosphonate scale and corrosion inhibitors include amino tri(methylene phosphonic acid); 1-hydroxyethane-1,1-diphosphonate; phosphate esters; and the like, and derivatives thereof.

The reaction of phosphonate ion to form orthophosphate using an oxidizing agent is referred to as a digestion reaction. The digestion reaction may be represented as follows:

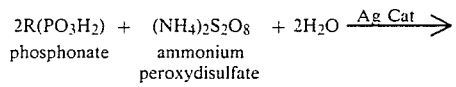

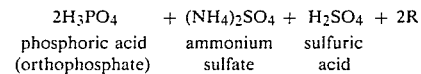

The reaction is usually complete at room temperature in less than 5 minutes. Waiting at least 10 minutes will assure complete reaction.

Any strong oxidizing agent may be used in the instant invention. Examples include perchloric acid, potassium permanganate, hydrogen peroxide, potassium dichromate, ozone, sodium bismuthate and ammonium peroxydisulfate (also known as ammonium persulfate). By strong oxidizing agent is meant, preferably, a stronger oxidizer than nitric acid.

Silver ion is added as a catalyst in the reaction. It is usually added as a soluble silver salt, for example silver nitrate, in aqueous solution. The dosage necessary, 8 ppb to 5000 ppm, is based on the silver ion introduced. Excess silver ion causes turbidity which interferes with the color of the solution. The silver, therefore, must be removed. The silver ion may be precipitated out of solution by the addition of 1000 to 50,000 ppm of reducing agent or at least an equimolar amount of a halide, preferably sodium chloride, usually in solution, based on the silver ion used. The precipitate may be removed by filtration.

Any reducing agent may be used. Examples include ascorbic acid, alkali metal sulfite and amino acid solutions.

The reducing agent is also necessary to form the blue orthophosphate/molybdate or vanadate complex. Therefore, if halide is added in Step (c), rather than reducing agent, reducing agent must be added in Step (d). Steps (c) and (d) may be conducted simultaneously.

The molybdate or vanadate is preferably added as an aqueous acid (pH 0.8 to 2) solution of ammonium molybdate or ammonium vanadate. The solution is added at a dosage of 5 to 30 percent, by volume, based on the volume of the sample being tested. 500 to 2000 ppm, based on the volume of the acid solution, of molybdate or vanadate ion is added to the acid solution. A color enhancing catalyst may be added. Examples include bismuth nitrate and ammonium potassium tartrate.

The amount of orthophosphate present is determined by an absorbance test. The orthophosphate forms a complex with the molybdate or vanadate ion. The complex gives a blue color to the solution in the presence of the reducing agent. The intensity of the blue color (625 to 880 nanometers) is proportional to the concentration. The intensity or absorbance may be measured by a spectrometer or colorimeter. The concentration of orthophosphate is determined from a calibration curve of phosphate versus absorbance. The curve may be prepared, for example, by adding to three samples the amount of molybdate or vanadate acid used in Step (d) to the same volume of solution used in Step (d) of demineralized water and 0, 1.0 and 2.0 ppm of orthophosphate and measuring the absorbance at the wavelength measured in Step (e). The curve is then prepared by plotting the orthophosphate concentration versus the absorbance.

The original aqueous solution may contain some orthophosphate. Therefore, the concentration of orthophosphate must be subtracted from the orthophosphate measured in the absorbance test, Step (e), since the orthophosphate present includes original orthophosphate. The original orthophosphate concentration may be measured by any method. For example, a reducing agent and molybdate or vanadate acid may be added to a portion of the original sample and the absorbance of the solution at 625 to 880 nanometers measured, Steps (c), (d) and (e).

The amount of orthophosphate determined from the calibration curve, minus any orthophosphate in the original aqueous sample, represents the total organic phosphonate concentration in the original aqueous sample.

The optimum range of phosphonate which may be measured by this test method are from 0 to 10 ppm phosphonate. If greater concentrations are found to be present, the accuracy may be improved by diluting the original sample.

EXAMPLES

Example 1

Solutions were prepared containing 1.0 ppm $PO_4^{-3}$ from amino tri(methylene phosphonic acid) (AMP) or 1-hydroxyethane-1,1-diphosphonic acid (HEDP). The solutions also contained 20 ppm chloride (from sodium chloride). (Sodium chloride was added in the Examples solely to show that salt which is often present in aqueous solutions will not interfere with the test results.) 80 ppm of soluble silver (from silver nitrate) and 4000 ppm ammonium peroxydisulfate were added to 25 ml aliquots of the solutions. After the solutions had reacted with the reagents for 20 minutes, 10 ppm chloride (from sodium chloride) were added to each solution in order to precipitate any excess soluble silver. The original 20 ppm chloride in the solution was considered in determining the amount of chloride necessary to precipitate the excess silver. Each solution was filtered through a Gelman 1.2 µm pore size Acrodisc syringe filter. 5.0 ml of color developer solutions (1.0 g bismuth nitrate, 5.6 g ammonium molybdate, 70 ml of sulfuric acid and 20,000 ppm ascorbic acid diluted to 1.0 liter) were added to each sample. After 5 minutes, the intensity (absorbance) of the color developed in each solution was measured using a Bausch and Lomb Spectronic Mini-20 at a wavelength of 700 nm in a one-inch path length cell. The absorbances of the solutions were then referred to a calibration graph, FIG. 1, (prepared from data obtained using orthophosphate standards) in order to obtain the final concentration results. The average of 6 results for AMP was 0.353 absorbance units which works out to be 1.02 ppm $PO_4^{-3}$. The average of six results for HEDP was 0.355 absorbance units or 1.03 ppm $PO_4^{-3}$.

Example 2

Standard solutions (calculated to contain 2.0 ppm $PO_4^{-3}$ following digestion) were prepared from amino tri(methylene phosphonic acid) (AMP) and 1-hydroxyethane-1,1-diphosphonate (HEDP). 2500 ppm soluble silver from silver nitrate) and 4000 ppm ammonium peroxydisulfate were added to 25 ml aliquots of the solutions. The solutions were allowed to digest for 20 minutes. Following digestion, 8000 ppm ascorbic acid were added to each solution in order to precipitate the excess soluble silver. The solutions were filtered through Gelman 5.0 µm pore size Acrodisc syringe filters. 5 ml of an acid molybdate solution (composed of 1.0 g bismuth nitrate, 5.6 g ammonium molybdate and 70 ml sulfuric acid diluted to 1 liter) were added to each solution. The absorbances of the solutions were measured 5 minutes later using a Bausch and Lomb Spectronic Mini-20 Spectrometer set at a wavelength of 700 nm and using a one-inch path length cell. The test results were obtained by referring to a calibration graph, FIG. 2, that had been prepared using data generated from orthophosphate standards that were carried through the procedure described.

The average of six tests performed on AMP was 0.74 absorbance units or 2.03 ppm $PO_4^{-3}$. The average of six tests performed on HEDP was 0.70 absorbance units or 1.92 ppm $PO_4^{-3}$.

Example 3

Standard phosphonate solutions (calculated to contain 1.0 ppm $PO_4^{-3}$ following digestion) were prepared from amino tri(methylene phosphonic acid) (AMP). The solutions also contained 525 ppm chloride (from sodium chloride). 2000 ppm soluble silver (from silver nitrate) and 8000 ppm ammonium peroxydisulfate were added to the solutions. The solutions were allowed to digest at room temperature for 20 minutes. Following digestion, 700 ppm chloride (from sodium chloride) were added to precipitate any excess soluble silver. The solutions were then filtered through Gelman 1.2 µm pore size Acrodisc syringe filters. 5 ml of an acid molybdate solution (composed of 1.0 g bismuth nitrate, 5.6 g ammonium molybdate and 70 ml sulfuric acid diluted to 1.0 liter) and 8000 ppm ascorbic acid were added to each solution. After 5 minutes, the absorbance of each solution was measured with a Bausch and Lomb Spectronic Mini-20 Spectrometer set at 700 nm and using a one-inch path length cell. The concentration results were obtained by referring the absorbance values for the solutions to a calibration graph, FIG. 3, that had been prepared using data generated from orthophosphate standards that had been carried through the procedure just described.

The average of three results for replicate measurements of AMP was 0.31 absorbance units or 0.98 ppm $PO_4^{-3}$.

Example 4

1.0 ppm $PO_4^{-3}$ (as 1-hydroxyethane-1,1-diphosphonate) was added to a cooling water sample that was known not to contain any organic phosphonates. 2000 ppm soluble silver (from silver nitrate) and 10,000 ppm ammonium peroxydisulfate were added to 10 ml of the sample. The sample was permitted to digest for 10 minutes. Following digestion, 700 ppm chloride (from sodium chloride) were added to precipitate any excess soluble silver. 5 ml of acid molybdate solution (composed of 1.0 g bismuth nitrate, 5.6 g ammonium molybdate and 70 ml sulfuric acid diluted to 1.0 liter) were added to the sample. The sample was then filtered through a Gelman 1.2 µm pore size Acrodisc syringe filter. The absorbance of the sample was measured after 5 minutes using a Bausch and Lomb Spectronic Mini-20 Spectrometer set at a wavelength of 700 nm and using a one-inch sample cell. The measurement represents the sum of orthophosphate and organic phosphonate concentration originally present in the sample.

A determination of the orthophosphate present in the sample was performed by analyzing a second aliquot of the sample in the same manner described above, except that no ammonium peroxydisulfate was used. The absorbance obtained (undigested sample) represents only the orthophosphate originally present in the sample.

The concentration results for the digested and undigested sample aliquots were obtained by referring the absorbance values obtained to a calibration graph that had been prepared using data generated from orthophosphate standards that had been carried through the digestion procedure described.

The orthophosphate concentration of the sample was 0.025 absorbance units or 0.08 ppm $PO_4^{-3}$ (the estimated detection limit under the conditions described). The sum of orthophosphate and organic phosphonate was 0.35 absorbance units or 1.06 ppm $PO_4^{-3}$. The difference between the digested and undigested sample (organic phosphonate) was 0.325 absorbance units or 0.98 ppm $PO_4^{-3}$.

What is claimed is:

1. A process for determining the amount of organic phosphonate present in an aqueous solution, comprising the steps of:
   (a) adding 1000 to 20,000 ppm of a strong oxidizing agent and 8 ppb to 5000 ppm silver ion as a reaction catalyst to the aqueous solution;
   (b) allowing the organic phosphonate present in said solution to react at room temperature to form orthophosphate;
   (c) precipitating any excess silver in said solution by the addition of 1000 to 50,000 ppm of a reducing agent or at least an equimolar amount of sodium chloride, based on the silver ion added in Step (a), and removing any precipitate formed;
   (d) adding to said solution 5 to 30 percent, by volume, of an acid solution containing 500 to 2000 ppm of ions selected from the group consisting of molybdate ion and vanadate ion, and if sodium chloride is used in Step (c), adding 1000 to 50,000 ppm of a reducing agent;
   (e) measuring the absorbance of said solution at 625 to 880 nanometers and determining the orthophosphate concentration from a calibration curve of orthophosphate concentration versus absorbance; and
   (f) subtracting any orthophosphate present in the original aqueous solution from the orthophosphate concentration determined in Step (e), to give the total organic phosphonate concentration.

2. The process of claim 1, wherein subsequent to adding an acid to said solution, Step (d), a color enhancing catalyst is added to said solution.

3. The process of claim 1, wherein said reducing agent is selected from the group consisting of ascorbic acid, alkali metal sulfite and amino acid solutions.

4. The process of claim 1, wherein said oxidizing agent is ammonium persulfate, said reducing agent is ascorbic acid, and said acid solution is molybdate solution.

5. The process of claim 1, wherein said strong oxidizing agent is a stronger oxidizer than nitric acid.

6. The process of claim 5, wherein said oxidizing agent is selected from the group consisting of perchloric acid, potassium dichromate, ozone, sodium bismuthate and ammonium persulfate.

* * * * *